United States Patent [19]

Fernholz et al.

[11] 4,093,559

[45] June 6, 1978

[54] PROCESS FOR THE PREPARATION OF A PALLADIUM CATALYST

[75] Inventors: Hans Fernholz, Fischbach, Taunus; Günter Roscher, Kelkheim, Taunus; Hans-Joachim Schmidt, Falkenstein, Taunus; Heinz Schmitz, Frankfurt am Main; Friedrich Wunder, Florsheim, Main, all of Germany

[73] Assignee: Hoechst Aktiengesellschaft, Frankfurt am Main, Germany

[21] Appl. No.: 663,117

[22] Filed: Mar. 2, 1976

[30] Foreign Application Priority Data

Mar. 4, 1975 Germany .................... 2509251

[51] Int. Cl.² ............... B01J 27/20; B01J 31/12; B01J 21/18; B01J 29/06
[52] U.S. Cl. ............... 252/443; 252/431 C; 252/447; 252/455 R; 252/455 Z; 252/460; 252/466 PT; 252/472; 252/473
[58] Field of Search ............ 252/473, 455 R, 455 Z, 252/443, 447, 460, 466 PT, 472, 431 C

[56] References Cited

U.S. PATENT DOCUMENTS

| 3,655,747 | 4/1972 | Sennewald et al. | 252/473 X |
|---|---|---|---|
| 3,759,839 | 9/1973 | Fernholz et al. | 252/431 C |
| 3,849,343 | 11/1974 | Hoekstra | 252/473 X |
| 3,862,252 | 1/1975 | Matsumura et al. | 252/473 X |
| 3,876,694 | 4/1975 | Gaenzler et al. | 252/473 X |
| 3,931,054 | 1/1976 | Lester | 252/472 X |
| 3,950,400 | 4/1976 | Fernholz et al. | 252/473 X |
| 3,998,759 | 12/1976 | Hoekstra | 252/455 X |

FOREIGN PATENT DOCUMENTS

| 1,901,289 | 9/1970 | Germany | 252/473 |
|---|---|---|---|
| 2,057,087 | 6/1972 | Germany | 252/473 |

*Primary Examiner*—Patrick P. Garvin
*Assistant Examiner*—William G. Wright
*Attorney, Agent, or Firm*—Curtis, Morris & Safford

[57] ABSTRACT

A process for the preparation of a palladium catalyst for the oxacylation of olefins in the gaseous phase, which comprises impregnating a catalyst carrier with a solution of a palladium compound drying the catalyst at a temperature of below 90° C until a residual solvent content of less than 8% by weight is attained, and reducing the impregnated catalyst with a gas mixture of inert gas and reducing agent.

17 Claims, No Drawings

PROCESS FOR THE PREPARATION OF A PALLADIUM CATALYST

The present invention relates to a process for the preparation of a palladium catalyst for the oxacylation of olefins in the gaseous phase, which catalyst contains palladium in reduced form. Such catalysts, described hitherto in different versions, are especially suitable for the oxyacylation of ethylene, propylene, 1-butene, 2-butene and isobutylene, and they are preferably used for the industrial-scale manufacture of vinyl acetate from ethylene. For example, in German Offenlegungsschrift No. 1,688,088, there is described a process for the manufacture of vinyl acetate by reaction in the gaseous phase of ethylene, acetic acid and oxygen, where a catalyst carrier, for example silicic acid, is impregnated with the solution of a palladium compound and a gold compound, for example sodium-palladium chloride and tetrachloro-auric(III) acid, dried, treated with a solution having a basic reaction, for example sodium hydroxide solution, dried again, impregnated with the aqueous solution of an alkali metal acetate, for example potassium acetate, and the noble metals fixed on the surface of the carrier grain in the form of their hydroxides or oxide hydrates are reduced either in the liquid phase for example with hydrazine hydrate, or in the gaseous phase, for example with ethylene. A catalyst prepared according to this process attains a space-time yield of 452 g of vinyl acetate per liter of catalyst and hour. A further improvement by means of a higher noble metal content cannot be obtained, and this is valid also for other known carrier catalysts containing palladiun in reduced form. Since for the profitability of a catalytic process the performance and activity of the catalyst is of decisive importance, the special disadvantage of the catalysts prepared by reduction of bivalent palladium as hitherto described resides in their limited performance due to the kind of their preparation.

The present invention, however, provides a process for the preparation of a palladium catalyst for the oxacylation of olefins in the gaseous phase, which comprises impregnating a catalyst carrier with a solution of a palladium compound and optionally of activators in an unsubstituted carboxylic acid, optionally in admixture with an inert solvent, drying the catalyst at a temperature of below 90° C until a residual solvent content of less than 8% by weight is attained, and reducing it in the gaseous phase at a temperature of from 40° to 260° C by passing a gas mixture containing an inert gas and a reducing agent over the catalyst.

The catalysts prepared according to this process excel by their performance and activity, and they have space-time yields of, for example, more than 1200 g of vinyl acetate per liter of catalyst and hour. Obviously, the process of the invention has an especially favorable influence on the formation of a palladium which catalyzes selectively the oxacylation of olefins in the gaseous phase.

The catalyst is especially suitable for the oxacylation of olefins of the formula $C_nH_{2n}$ having from 2 to 12 carbon atoms, preferably from 2 to 4 carbon atoms, in the molecule by reaction with unsubstituted, saturated, aliphatic monocarboxylic acids having up to 10 carbon atoms in the molecule which are vaporizable under the reaction conditions, preferably those having from 2 to 5 carbon atoms in the molecule, i.e. acetic, propionic, n- and isobutyric acid, or the various valeric acids.

Suitable catalyst carriers are all inert substances which maintain their mechanical stability under the reaction conditions, for example silicic acid, silica acid, silica gel, alumosilicates, active charcoal, aluminum oxide, spinels, zirconium oxide, pumice or silicium carbide. With respect to their physical properties, the catalyst carriers may vary within a wide range. For example, a silicic acid having a surface of from 40 to 300 $m^2/g$ and a mean pore diameter of from 50 to 2000 A is suitable as carrier material.

As unsubstituted carboxylic acids to be used as solvents for the palladium compound and optionally the activators, there may be employed above all those having up to 10 carbon atoms in the molecule, for example acetic, propionic, n- and isobutyric acid, or the various valeric acids. Because of its physical properties and for economic reasons, acetic acid is the preferred solvent. An inert solvent may be used in addition in those cases where the palladium compound is not sufficiently soluble in the carboxylic acid. For example, palladium chloride is more easily dissolved in aqueous acetic acid than in glacial acetic acid. There may be employed those solvents in addition which are inert to the palladium compound and miscible with the carboxylic acid, for example, apart from water, ketones such as acetone or acetylacetone, ethers such as tetrahydrofuran or dioxan, and also hydrocarbons such as benzene.

As palladium compounds there may be used all salts and complexes which are soluble and reducible and do not leave deactivating substances such as halogen or sulfur in the complete catalyst. Especially suitable are palladium carboxylates, preferably the salts of aliphatic monocarboxylic acids having from 2 to 5 carbon atoms, for example the acetate, propionate or butyrate. Furtherore, there are suitable the following compounds: palladium nitrate, palladium nitrite, palladium oxide hydrate, palladium oxalate, palladium succinate, palladium benzoate, palladium salicylate, palladium tropolonate, palladium acetylacetonate, palladium acetoacetate. But also compounds such as palladium sulfate or the halides of palladium may be used; it must however be ensured that the sulfate radical is removed before the impregnation, for example by precipitation with barium acetate, as well as the halogen, for example by precipitation with silver nitrate, so that the sulfate or halogen anion is not contacted with the carrier. Because of its solubility and because it is easily obtainable, palladium acetate is the preferred palladium compound.

Generally, the palladium content of the catalyst is from 0.5 to 5% by weight calculated on the total mass of the carrier catalyst (the percentage taking into account only the metal portion of the palladium compound).

The catalyst carrier may be impregnated by soaking the carrier material with the solution of the palladium compound and subsequently pouring off or filtering off the solution in excess. In order to avoid solution losses, it is advantageous to use that amount of solution only which corresponds to the integral pore volume of the carrier, and to ensure a careful intermixing, so that all particles of the carrier material are uniformly wetted. Intermixing may be carried out by means of an agitator. It is advantageous to carry out impregnation and intermixing simultaneously, for example in a revolving drum or a tumbling drier, where drying may follow immediately. It is also advantageous to choose the amount and the composition of the impregnating solution in such a manner that it corresponds to the pore volume of the carrier material and that the carrier is impregnated with the desired amount of active substances in one impregnation step only.

The solution used for impregnating the catalyst carrier, apart from the palladium compound, contains advantageously salts and compounds of other metals in addition, which have an activating, promoting or cocatalyzing effect. Activating or cocatalyzing additives for the oxacylation of olefins according to this invention are for example alkali metal carboxylates or alkaline earth metal carboxylates such as potassium acetate, sodium acetate, lithium acetate, sodium propionate, calcium isobutyrate magnesium acetate; suitable are also those alkali metal or alkaline earth metal compounds which are converted to carboxylates under the reaction conditions, for example hydroxides, oxides or carbonates. Suitable activating or cocatalyzing additives are furthermore those salts, compounds or complex compounds of cadmium, gold, bismuth, copper, manganese, iron, cobalt, cerium, vanadium or uranium which contain no halogen or sulfur, for example carboxylates, oxides, hydroxides, carbonates, citrates, tartrates, nitrates, acetylacetonates, benzoylacetonates, acetacetates, acetoaurates. Especially appropriate are cadmium acetate, bismuth acetate, copper acetylacetonate, barium acetoaurate, iron citrate. Mixtures of different additives may also be used. Each activator is generally added in an amount corresponding to 0.01 to 4% by weight of the respective metal component, calculated on the total mass of the carrier catalyst.

The special advantage of the process of the invention resides in the fact that all active substances are applied to the carrier in one single step.

Drying of the catalyst carrier impregnated with the solution of the active substances is preferably carried out under reduced pressure. It is furthermore generally recommended to carry out the drying in an inert gas current, for example in a nitrogen or carbon dioxide current. The residual solvent amount is less than 8% by weight, preferably less than 6% by weight.

The last step of the process of the invention, that is, the reduction of the palladium compound, may be carried out under reduced, normal or elevated pressure of up to 10 bars. The reducing agent should be the more diluted with an inert gas the higher the pressure. The reduction temperature is in a range of from 40° to 260° C, preferably from 70 to 200° C. Generally, it is recommended to use an inert gas/reducing agent mixture which contains from 0.01 to 50% by volume, preferably from 0.5 to 20% by volume of reducing agent. As inert gas, there may be used nitrogen, carbon dioxide, noble gases or paraffin-hydrocarbons such as methane, ethane, propane, isobutane or butane. Suitable reducing agents are for example hydrogen, methanol, formaldehyde, ethylene, propylene, isobutylene, butylene or other olefins. The amount of reducing agent depends on the oxidation equivalent of the palladium and on that of the gold if used as activator; the reduction equivalent should be at least 1 to 1.5 times that of the oxidation equivalent, larger amounts of reducing agent not being critical. For example, at least 1 mol of hydrogen should be used per mol of palladium. The reduction may be carried out immediately after drying in the same apparatus. The preferred operation mode for the process of the invention is to carry out the reduction in the reactor serving for the oxacylation of the olefin, that is, in the starting period of the oxacylation. It is therefore advantageous to use the olefin to be oxacylated also as reducing agent.

The reduced palladium must not necessarily be present in the form of palladium metal.

The process of the invention is therefore distinguished by simple technological execution and the formation of especially active catalysts.

Oxacylation is carried out generally by passing carboxylic acid, olefin and oxygen or oxygen containing gases over the complete catalyst, at a temperature of from 100° to 250° C, preferably from 120° to 220° C, and under a pressure of from 1 to 25 bars, preferably from 1 to 20 bars; non-reacted components optionally being recycled. It is advantageous to choose concentration ratios which ensure that the reaction mixture is maintained outside the interval determined by the known explosion limits. Preferably, the oxygen concentration is kept low, for example, in the case where ethylene is used, below 8% by volume (relative to the acetic acid-free gas mixture). Under certain conditions, a dilution with inert gases such as nitrogen or carbon dioxide is recommended. $CO_2$ is especially suitable as diluting agent in the case of cyclic processes, since it is formed in small amounts during the reaction.

The following examples illustrate the invention; percentages being by weight unless otherwise stated. N is Nl and $Nm^3$ stands for "normal," that is, at 0° C and 760 mm Hg.

EXAMPLE 1

A solution of 28.8 g of palladium acetate, 26.8 g of potassium acetate, 23.4 g of cadmium acetate, 1.8 g of manganese acetate and 340 ml of acetic acid is applied to 500 g of a silicic acid carrier (= 1 l) having a surface of 120 m$^2$/g and a pore volume of 0.8 ml/g, and dried at 60° C and 200 torrs under a nitrogen atmosphere. As soon as the weight of the catalyst is no longer decreasing, 10% of hydrogen are added to the nitrogen until a total of 4 Nl of hydrogen (= 1.4 mol of $H_2$/mol of Pd) has passed over the catalyst, and subsequently, flushing is carried out with nitrogen. The complete catalyst contains 2.3% of palladium, 1.7% of cadmium, 1.9% of potassium and 0.07% of manganese.

The catalyst is introduced into a reaction tube having an inner diameter of 30 mm. Under a pressure of 9 bars (reactor inlet) and at a catalyst temperature of 175° to 178° C, a gas current of 4.5 Nm$^3$ per hour is passed over the catalyst, the gas containing 60.8% by volume of ethylene, 15.5% by volume of inert gas ($N_2$ and $CO_2$), 17.4% by volume of acetic acid and 6.3% by volume of oxygen. A space-time yield of from 1180 to 1210 g of vinyl acetate per liter of catalyst and hour is obtained, which is unchanged even after 600 hours.

EXAMPLE 2

500 g of the carrier indicated in Example 1 are impregnated with a solution of 24.4 g of palladium acetate, 23.4 g of cadmium acetate, 26.6 g of potassium acetate, 1.8 g of manganese acetate and 340 ml of acetic acid, and dried as described in Example 1. After drying, the catalyst is heated to 160° C in a tubular stove under an ethane inert gas atmosphere and normal pressure, subsequently, the ethane is passed through a washing bottle preceding the stove and containing methanol of 20° C, until 3 g of methanol have passed over the catalyst (= 1 mol of methanol/mol of palladium). The reduced catalyst is cooled in the ethane current; it contains 2% of palladium, 1.7% of cadmium, 1.9% of potassium and 0.07% of manganese.

Under the conditions as described in Example 1, this catalyst has a space-time yield of 1050 to 1070 g of vinyl acetate per liter of catalyst and hour.

EXAMPLE 3

As described in Example 1, 500 g of the carrier indicated there are impregnated with a solution of 19 g of palladium acetate, 23.4 g of cadmium acetate, 26.6 g of potassium acetate, 1.8 g of manganese acetate and 340 ml of acetic acid (containing 30% of water), and dried. After drying, the catalyst is reduced at 180° C in the oxacylation reactor described in Example 1 with a mixture of 1% of ethylene and 99% of nitrogen. The complete catalyst contains 1.5% of palladium, 1.7% of cadmium, 1.9% of potassium and 0.07% of manganese.

After reduction, ethylene, inert gases, acetic acid and oxygen as passed over the catalyst under the conditions and in the amounts indicated in Example 1. The space-time yield is 735 – 750 g of vinyl acetate per liter of catalyst and hour.

EXAMPLE 4

As described in Example 1, 500 g of the carrier indicated there are impregnated with a solution of 9 g of palladium acetate, 23.4 g of cadmium acetate, 26.6 g of potassium acetate, 1.8 g of manganese acetate in 345 ml of acetic acid, and dried. After drying, the catalyst is heated to 100° C in a $CO_2$ current under normal pressure, subsequently, 1% of butylene are added to the $CO_2$ until 10 Nl of butylene are passed over the catalyst (= 10 mol of butylene/1 mol of palladium). The complete catalyst is allowed to cool in the $CO_2$ current; it contains 0.7% of palladium, 1.7% of cadmium, 1.9% of potassium and 0.07% of manganese.

Examined under the conditions as described in Example 1, the catalyst has a space-time yield of 470 – 505 g of vinyl acetate per liter of catalyst and hour.

EXAMPLE 5

530 g of a silicic acid carrier having a surface of 180 $m^2/g$ and a pore volume of 0.7 ml/g are impregnated with a mixture of a solution of 24.4 g of palladium acetate, 26.6 g of potassium acetate in 200 ml of acetic acid and a solution of 34.6 g of freshly precipitated barium aurate (4.6 g of barium aurate and 30 g of water) in 140 ml of acetic acid, and dried as indicated in Example 1. The dry catalyst is heated to 160° C in a nitrogen current under a pressure of 4 bars, and subsequently reduced with $N_2/H_2$ (99% / 1%) before it is allowed to cool in a nitrogen current. The complete catalyst contains 2% of palladium, 0.5% of gold and 1.9% of potassium.

Under the conditions as described in Example 1, this catalyst has a space-time yield of 950 g of vinyl acetate per liter of catalyst and hour.

EXAMPLE 6

500 g of the silicic acid carrier as described in Example 1 are impregnated with a solution of 30.5 g of vanadylacetylacetonate in 360 ml of acetic acid (containing 50% of water), and dried. Subsequently, 24.4 g of palladium acetate and 26.6 g of potassium acetate are dissolved in 340 ml of acetic acid and applied to the carrier. After drying, the catalyst is heated to 200° C in a nitrogen current (20 l $N_2$/h), and subsequently, the nitrogen is passed through a preceding washing bottle containing methanol warmed to 20° C, until 6 g methanol are evaporated. Subsequently, the catalyst is allowed to cool to room temperature in the nitrogen current (without methanol). The complete catalyst contains 2% of palladium, 1.9% of potassium and 0.9% of vanadium. Under a pressure of 7.5 bars (reactor inlet) and at a catalyst temperature of 180° C, 2.6 $Nm^3/h$ of a gas mixture containing 41.6% by volume of propylene, 32.2% by volume of inert gas (nitrogen and carbon dioxide) 19.0% by volume of acetic acid and 7.2% by volume of oxygen are passed over 1 l of the catalyst. A space-time yield of 940 – 950 g of allyl acetate is obtained per liter of catalyst and hour.

EXAMPLE 7

500 g of an active charcoal prepared from pit coal and having a surface of 700 $m^2/g$ and a pore volume of 1.1 ml/g are impregnated with a mixture of a solution of 24.4 g of palladium acetate, 20 g of bismuth acetate, 26.6 g of potassium acetate in 350 ml of acetic acid and a solution of 34.6 g of freshly precipitated barium aurate (4.6 g of barium aurate and 30 g of water) in 100 ml of acetic acid, and dried. Nitrogen (100 l/h) containing 1% of isobutylene is passed for 20 hours at 40° C over the dried catalyst. The complete catalyst contains 2% of palladium, 0.5% of gold, 1.6% of bismuth and 1.9% of potassium.

1 l of this catalyst is introduced into the reactor described in Example 1. Under a pressure of 7 bars (reactor inlet) and at a catalyst temperature of 180° C, 2400 Nl of isobutylene, 1600 g of acetic acid and 200 Nl of oxygen are passed per hour over the catalyst, and 620 – 640 g of methallyl acetate are obtained.

What is claimed is:

1. A process for the preparation of a palladium catalyst for the oxacylation of olefins in the gaseous phase, which comprises impregnating a catalyst carrier with a solution comprising a palladium compound dissolved in an unsubstituted carboxylic acid, drying the catalyst at a temperature below 90° C until a residual solvent content of less than 8% by weight is attained, and thereafter reducing the catalyst in a gaseous phase at a temperature of 40° to 260° C by passing a gas mixture containing an inert gas and a reducing agent over the catalyst.

2. The process as claimed in claim 1, which comprises using silicic acid, silica gel, silicates, alumosilicates, active charcoal, aluminum oxide, spinels, zirconium oxide, pumice or silicium carbide as catalyst carrier.

3. The process as claimed in claim 1, wherein the carboxylic acid used as solvent for the palladium compound, contains up to 10 carbon atoms.

4. The process as claimed in claim 1, which comprises using a carboxylate of palladium as the palladium compound.

5. The process as claimed in claim 1, wherein the palladium content of the catalyst is from 0.5 to 5% by weight, calculated on the total mass of the carrier catalyst.

6. The process as claimed in claim 1, which comprises using the carboxylates of alkali or alkaline earth metals as activators.

7. The process as claimed in claim 1, which comprises using each single activator in an amount corresponding to 0.01 to 4% by weight of the respective metal, calculated on the total mass of the carrier catalyst.

8. The process as claimed in claim 1, which comprises drying the impregnated catalyst carrier under reduced pressure.

9. The process as claimed in claim 1, wherein the residual solvent content of the catalyst is less than 6% by weight.

10. The process as claimed in claim 1, wherein the reduction temperature is from 70° to 200° C.

11. The process as claimed in claim 1, wherein the mixture of reducing agent and inert gas contains from 0.01 to 50% by volume of reducing agent.

12. The process as claimed in claim 1, which comprises carrying out the reduction of the catalyst in the reactor in which the olefin is oxacylated.

13. The process as claimed in claim 12, which comprises using the olefin to be subsequently oxacylated as reducing agent.

14. The process of claim 1 wherein said solution contains dissolved therein an activator for said catalyst.

15. The process of claim 1 wherein the catalyst solution includes an inert solvent.

16. In a process for the preparation of a palladium catalyst supported on a carrier which is suitable for the oxacylation of olefins in the gaseous phase, the improvement comprising impregnating the carrier with a solvent solution of an unsubstituted carboxylic acid containing a palladium compound dissolved therein, drying the impregnated carrier at a temperature below 90° C to a residual solvent content of less than 6% by weight and thereafter reducing the palladium at a temperature of 70° to 200° C. in an inert gas atmosphere containing a reducing agent.

17. The process of claim 16 wherein the carboxylic acid is acetic acid.

* * * * *